(12) United States Patent
Scoles et al.

(10) Patent No.: US 9,958,463 B2
(45) Date of Patent: May 1, 2018

(54) METHOD FOR DETECTING CIRCULATING TUMOUR CELLS (CTCS)

(71) Applicants: UNIVERSITÀ DEGLI STUDI DI UDINE, Udine (IT); STICHTING KATHOLIEKE UNIVERSITEIT, Nijmegen (NL)

(72) Inventors: Giacinto Scoles, Duino Aurisina (IT); Fabio Del Ben, Azzano Decimo (IT); Matteo Turetta, Mestre (IT); Wilhelm Huck, Beek Ubbergen (NL); Aigars Piruska, Nijmegen (NL)

(73) Assignees: UNIVERSITÀ DEGLI STUDI DI UDINE, Udine (IT); STITCHING KATHOLIEKE UNIVERSITEIT, Nijmegen (NL)

( * ) Notice: Subject to any disclaimer, the term of this patent is extended or adjusted under 35 U.S.C. 154(b) by 32 days.

(21) Appl. No.: 15/106,727

(22) PCT Filed: Dec. 18, 2014

(86) PCT No.: PCT/IB2014/067057
§ 371 (c)(1),
(2) Date: Jun. 20, 2016

(87) PCT Pub. No.: WO2015/092726
PCT Pub. Date: Jun. 25, 2015

(65) Prior Publication Data
US 2017/0003306 A1    Jan. 5, 2017

(30) Foreign Application Priority Data

Dec. 19, 2013 (IT) .............................. RM2013A0700

(51) Int. Cl.
*G01N 33/84* (2006.01)

(52) U.S. Cl.
CPC ..... *G01N 33/84* (2013.01); *G01N 2800/7028* (2013.01)

(58) Field of Classification Search
CPC ... C12N 5/00; G01N 33/84; G01N 2800/7028
See application file for complete search history.

(56) References Cited

U.S. PATENT DOCUMENTS

2013/0224789 A1    8/2013  Tirosh et al.
2014/0255972 A1    9/2014  Tirosh et al.

OTHER PUBLICATIONS

International Search Report issued in PCT/IB2014/067057, four pages, dated Mar. 23, 2013.
Written Opinion of the ISA issued in PCT/IB2014/067057, five pages, dated Mar. 23, 2013.
San Martín Alejandro et al. "A Genetically Encoded FRET Lactate Sensor and Its Use to Detect the Warburg Effect in Single Cancer Cells" *PLOS ONE*, vol. 8, No. 2, e57712 (Feb. 2013).
Suzuki et al. "Detection of Single Cell Activity by Using Fluorescence-Based Multiscale pH and Oxygen Sensors" *International Symposium on Micro-Nanomechatronics and Human Science*, IEEE, pp. 311-316 (Nov. 2008).

*Primary Examiner* — Ruth A Davis
(74) *Attorney, Agent, or Firm* — Nixon & Vanderhye PC

(57) ABSTRACT

The present invention relates to a method for detecting circulating tumor cells (CTCs) in body fluids, preferably in blood and lymph.

In particular, the method for detecting circulating tumor cells in a body fluid comprises a step of detecting a change in pH and/or in a concentration of at least one molecule selected from lactic acid, lactate ions and protons within an isolated volume of said body fluid in which a cell has been encapsulated.

11 Claims, 6 Drawing Sheets

METHOD FOR DETECTING CIRCULATING TUMOUR CELLS (CTCS)

This is the U.S. national phase of International Application No. PCT/IB2014/067057, filed Dec. 18, 2014, which designated the U.S. and claims priority to Italian Application No. RM2013A000700, filed Dec. 19, 2013; the entire contents of each of which are hereby incorporated by reference.

FIELD OF THE INVENTION

The present invention relates to a method and an apparatus for detecting circulating tumour cells (CTCs) in body fluids, preferably in blood and lymph.

In particular, the method for detecting circulating tumour cells in a body fluid comprises a step of detecting a change in pH and/or in a concentration of at least one molecule selected from lactic acid, lactate ions, protons within an isolated volume of said body fluid in which a cell has been encapsulated

BACKGROUND TO THE INVENTION

Nowadays, there is widespread agreement that the possibility of detecting and counting the CTCs can lead to important information in medical field.

In particular, this information can be used for defining a diagnosis, a treatment and a monitoring system of many forms of cancer.

Some known procedures for isolating and detecting the CTCs from blood include, for example, the use of magnetic beads coated with specific antibodies capable of recognizing specific cell-surface markers. Examples of commercial technologies based on an antibodies/surface markers interaction include the CellSearch System™ manufactured by Veridex.

However, the use of surface proteins as targets for isolating and detecting CTCs suffers from different problems which are, for example, a lack of unique biomarkers on CTCs, the exclusively isolation/detection of EpCAM+ epithelial cells and the impossibility to use the isolated cells for further analysis. Further problems linked to this approach are the slow speed (with CellSearch System™ only 8 analyses per day can be carried out) and high cost (about 350$ per analysis of materials only, 650$ including technical assistance in performing the analysis [Data by Istituto Oncologico Veneto, Padova]) due to the fact that purified antibodies are required for the isolation/detection.

Other known methods for detecting CTCs use physical properties (such as size or hardness) to discriminate tumour cells from non-tumour cells. These methods, however, has not been clinically validated.

Reviews of the current technology for detecting CTCs can be found in: "Circulating Tumour Cells: Liquid Biopsy of Cancer, C. Alix-Panabieres and K. Pantel, Clinical Chemistry 59: 1,110-118 (2013); and "Techniques for Label-Free Separation of Circulating Tumour Cells: from Historical Foundations to Recent Developments", C. Jin et al, Lab Chip, 2013, DOI:10.1039/C3LC50625H.

Therefore, there is a huge need of developing alternative approaches capable of improving the detection of Circulating Tumour Cells that allow to overcome the drawbacks of the methods described in the state of the art.

SUMMARY OF THE INVENTION

The technical problem solved by the present invention is then to provide a method which allow to detect and isolate the CTCs in a body fluid by using an alternative approach that allow to overcome the drawbacks mentioned above.

Part of the work leading to this invention has received funding from the European Research Council under the European Union's Seventh Framework Programme (FP7/2007-2013)/ERC grant agreement no. 269051

The invention is based on the observation that the biochemistry of tumour cells is different to that of normal cells. More in particular, in aerobic conditions most cancer cells display a phenomenon known as Warburg effect, (Koppenol, W. H., P. L. Bounds, and C. V. Dang, *Otto Warburg's contributions to current concepts of cancer metabolism*. Nat Rev Cancer, 2011. 11(5): p. 325-37), that is, high rate of glycolysis in the cytosol with lactate production even in the presence of oxygen, in comparison with normal cells that have a low rate of glycolysis, oxidation of pyruvate in mitochondria and no production of lactates. To avoid acidification of intracellular pH, glycolytically-produced acid must be extruded by tumour cells through several proton transporters, such as V-ATPase, the Na+/H+ exchanger (NHE), the carbonic anhydrases, the proton linked monocarboxylate transporter MCTs, the Cl-/HCO3-exchangers and ATP synthase. The increased activity of these transporters causes reversal of the normal intra-extracellular pH gradients, so that cancer cells produce significant acidification of the extracellular microenvironment, while they maintain internally a normal or slightly alkaline pH.

In a relatively recent study on a tumour cell line metabolism, it was shown that single tumour cells secrete up to $3.68 \times 10^{-13}$ moles acid per hour (DeBerardinis, R. J., et al., "*Beyond aerobic glycolysis: transformed cells can engage in glutamine metabolism that exceeds the requirement for protein and nucleotide synthesis*", Proc Natl Acad Sci USA, 2007, 104(49): p. 19345-50).

The secretion of acids by rare tumour cells in body fluid such as blood cannot be detected directly as the protons become extremely diluted in the plasma.

Although this change in the extracellular environment cannot be detected the inventors have observed that when a tumour cell is isolated in a very small volume, changes in the chemical composition within said volume and resulting from the different biochemistry of the tumour cell can be significantly detected.

Thus, in one aspect the invention described herein relates to a method for detecting circulating tumour cells as defined in claim 1.

More in particular, the method for detecting circulating tumour cells (CTCs) in a body fluid comprises the following steps:
- encapsulating a cell in a volume of about 10 pL to 10 nL of said fluid;
- incubating said volume at a temperature of from 4° C. and 37° C. for at least 1 minute;
- detecting a change in pH and/or in a concentration of at least one molecule selected from lactic acid, lactate ions, protons within said incubated volume, wherein a decrease in said pH and/or an increase in the concentration of said at least one molecule, with respect to a pH and/or a concentration determining for the same volume before said incubation step, indicates the presence of circulating tumour cells in said body fluid.

Other advantages and features of the present invention will be evident from the following detailed description of same embodiments of the invention.

BRIEF DESCRIPTION OF THE DRAWINGS

FIG. 5B refers to triple negative breast cancer cells; FIG. 5C to cells from breast metastatic carcinoma; FIG. 5D to cells from colorectal adenocarcinoma.

DETAILED DESCRIPTION OF THE INVENTION

Figures 1A, 1B:
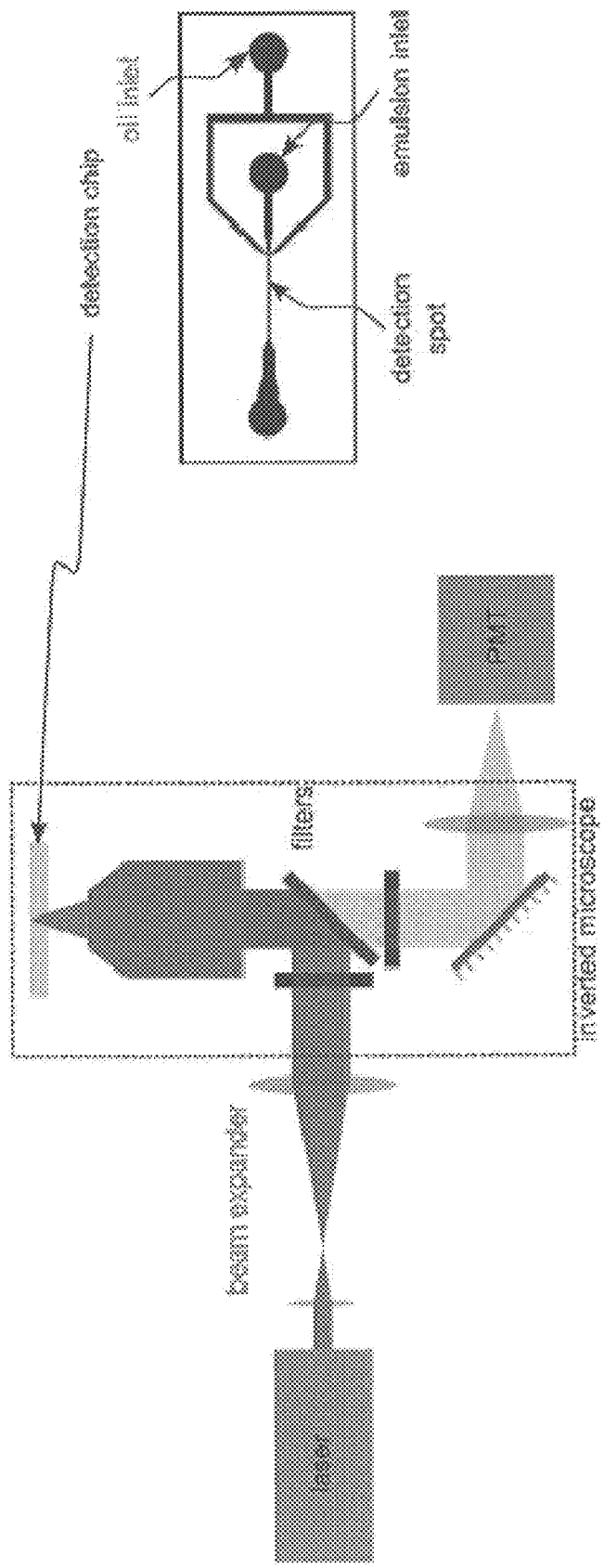
FIGS. 1a and 1b show, respectively a microfluidic chip and a fluorescence sensing device for implementing an embodiment of a method according to the invention.

The invention relates to a method and an apparatus for detecting circulating tumour cells (CTCs) in body fluids.
Method for Detecting Circulating Tumour Cells (CTCs)

The method for detecting circulating tumour cells in a body fluid, as already indicated above, comprises the following steps:
  encapsulating a cell in a volume of about 10 pL to 10 nL of said fluid;
  incubating the isolated volume at a temperature of from 4° C. and 37° C. for at least 1 minute;
  detecting a change in pH and/or in a concentration of at least one molecule selected from lactic acid, lactate ions and protons within said incubated volume,
wherein a decrease in said pH and/or an increase in the concentration of said at least one molecule, with respect to a pH and/or a concentration determining for the same volume before said incubation step, indicates the presence of circulating tumour cells in said body fluid.

The method of the invention can also comprise a step of dilution of the volume of body fluid with water or salt-containing buffers.

In a preferred embodiment of the invention, the isolated volume is in form of a droplet within a droplet-based microfluidic device. In the present description the expression "isolated volume" and "encapsulated volume" are interchangeable.

The droplet microfluidic device enables the manipulation of discrete fluidic packets in the form of picoliter droplets and addresses the need for lower costs, higher throughout and higher sensitivities at which the assays can be performed. The technique is well adapted to perform operations and manipulations in series, like encapsulation and screening. In particular, droplet microfluidic device allows to screen individual droplets using fluorescence-based techniques or mass spectrometry, to sort droplets from other droplets, to store them, to re-inject them into other microfluidic devices, to fuse droplets with other droplets and to culture cells in droplets. Thus, by encapsulating all cells, for example, from 1 mL to 10 mL of blood into individual droplets, CTCs can be easily isolated thus providing inexpensive diagnostic applications and single cells for further studies.

In particular, the droplets can be part of an aqueous emulsion in a microfluidic device. In one embodiment the droplet is in a water-in-oil emulsion (W/O emulsion), but in principle a double emulsion may be employed. The emulsion can be formed on-chip or separately. Since the Warburg effect occurs mainly in aerobic conditions, it can be advantageous to employ as oil component of the emulsion a fluorous oil which helps to store dissolved oxygen. Furthermore, a surfactant can be added to the fluorous oil. Suitable fluorous oil as those described in the state of the art such as, for example, FC-77 and FC-40 from 3M™.

The method of the invention, as above indicated, is carried out to detect CTCs in body fluids. In one embodiment of the invention, said body fluid is selected form the group comprising blood, serum, lymph, pleural fluid, peritoneal fluid, cerebrospinal fluid. In a preferred embodiment, the body fluid is blood.

In case of blood that can contain about $4-11\times10^6$ of white blood cells per ml and $10^9$ red blood cells, the method can also comprise a step of removing of red blood cells in order to accelerate throughput.

The method of the invention also comprises a step of incubation of the isolated (encapsulated) volume. More in particular, the step of incubation can be carried out at a temperature of from a room temperature to 37° C.

The incubation time can be from at least one minute to 48 h. In particular, it can be of at least one minute in the case of lactate or pH detection. These time can vary with tuning of the conditions (E.g.: mediums) in which cells are managed.

The incubation step can be carried out either on-chip or off-chip.

A rough calculation of the influence of secreted protons (lactic acid partially dissociates in water into the lactate anion and $H^+$) into a volume of 100 pL shows that even after a short period of incubation, the pH of isolated volume decreases. In particular, the inventors observed that a $H^+$ secretion of about $3.68\times10^{-13}$ moles per 100 pL volume in 1 h would result in a concentration change of about 3.68 mM, which if one started with pure water, would lead to a drop of pH from pH 7 to pH 2.4 after 1 hour incubation.

As previously mentioned, according to one embodiment of the method herein described the presence of CTCs in a body fluid can be shown by detecting a change in pH value within the isolated volume after the incubation step. This change can be detected by using any technique known to the skilled person in the art being suitable for detecting a change in pH values.

The change in pH values can be determined by a pH-indicator.

The pH-indicator can be either pH-sensitive dye or an indicator that changes its absorption/emission spectrum while the pH changes. Examples of these indicators are pHrodo™ Green (Life Technologies), which fluoresces green at acidic pH, SNARF®-4F 5-(and-6)Carboxylic acid (Life Technologies), with the ratio between 580 nm and 640 nm fluorescence increasing at acidic pH, and pH-sensitive inorganic salt which aggregates to form microcrystals.

Furthermore, the method can also comprise a step of irradiating the incubated volume by a laser in the excitation wavelength of the dye in order to detect the signal of the pH-indicator. It can be appreciated that, even in this embodiment, the change in pH values is function of the signal emitted after irradiation.

As above indicated, the detection of CTCs can be also carried out by determining the concentration of at least one molecule selected from lactic acid, lactate ions and protons (lactic acid partially dissociates in water into the lactate anion and $H^+$) within the incubated volume. The concentration can be determined by using any technique known to the skilled person for such a purpose. As way of example the lactic acid can be determined by fluorescent indicators (Fluoro lactate detection kit by Cell Technology, Inc.).

Still further alternatively detection may be based on the mechanical properties of a droplet and/or on detection of a change of viscosity of the contents, in which case the indicator may comprise a monomer which undergoes pH-induced polymerisation. Depending upon the monitored secretion (or absorption) other indicators may also be employed.

The method can also comprise a step of sorting out the isolated volume comprising the detected CTCs in order, for example, to culture the circulating tumour cells, or to characterize it from a genetic or proteomic point of view, or for drug-screening purposes.

Apparatus for Detecting Circulating Tumour Cells (CTCs)

There is disclosed herein also an apparatus for detecting circulating tumour cells (CTCs).

In particular, the apparatus for detecting circulating tumour cells in a body fluid comprises:
- means for encapsulating a cell in a volume of about from 10 pL to 10 nL;
- means for detecting a change in pH and/or in a concentration of at least one molecule selected from lactic acid, lactate ions, protons within said incubated volume. In one embodiment of the invention, said means for isolating the volume is a droplet-based microfluidic device.

As already described above with reference to the method, the volume of a droplet can be in the range pL to nL, for example less than 10 nL, 5 nL, 1 nL or 500 pL; a preferred volume is, in embodiments, of order 100 pL. In a microfluidic device the maximum dimension of a channel is preferably less than 1,000, 500, 300, 200 or 100 micrometers.

In one embodiment the droplet is an aqueous droplet in a water-in-oil emulsion (W/O emulsion) within the microfluidic device. The emulsion can be formed on-chip or separately. Since the Warburg effect occurs mainly in aerobic conditions, it can be advantageous to employ as oil component of the emulsion a fluorous oil which helps to store dissolved oxygen. Preferably a surfactant is added to the fluorous oil. Suitable fluorous oil as those described in the state of the art such as, for example, FC-77 and FC-40 from 3M™.

In one embodiment of the invention said means for detecting comprises a pH-sensitive dye and/or an indicator that changes its adsorption spectrum while the pH changes. Examples of these indicators are pHrodo™ Green (Life Technologies), which fluoresces green at acidic pH (Life Technologies), SNARF®-4F 5-(and-6)Carboxylic acid (Life Technologies), with the ratio between 580 nm and 630 nm fluorescence increasing at acidic pH, and pH-sensitive inorganic salt which aggregates to form microcrystals.

In one embodiment of the invention said means for detecting can be means capable of determining the concentration of at least one molecule selected from lactic acid, lactate ions, protons within said incubated volume (lactic acid partially dissociates in water into the lactate anion and $H^+$) within the incubated volume. As way of example the lactic acid can be determined by fluorescent indicators (Fluoro lactate detection kit by Cell Technology, Inc.).

In one embodiment, the detection means can be also included directly in the droplets. The detection of changes in pH values within the droplet can be also performed by passing the droplets through a channel in the microfluidic device comprising a sensing device, for example, a fluorescent sensing arrangement.

Furthermore, the apparatus can comprises a laser capable of emitting wavelength in the excitation range of the fluorophore in order to detect the signal of the pH-indicator. It can be appreciated that, even in this embodiment, the change in pH values is function of the signal emitted after irradiation. The apparatus can comprises a detector such as a photomultiplier.

Experimental Examples

1. Materials

PhRodo Green (Invitrogen Inc.), pH-sensitive dye, fluorescence green at acidic pH Fluoro Lactate Detection Kit (Cell Technology, Inc.)

D-glucose (Sigma-Aldrich)

HFE-7500 (3M Inc)

FC-40 (3M), fluorinated oil

PBS (phosphate-buffered saline) buffer 0.9% NaCl solution in DI water

PDMS (polydimethylsilicone) kit (Dow Corning)

SNARF-5F or 4F (Invitrogen)

2. Solutions

Oil phase: 2% (w/w) of SS01 in HFE-7500 (a hydrofluroether solvent)

Dye stock: 1 mg/ml pHrodo Green (Invitrogen Inc.) in DI (deionised) water;

Dye stock: 2 mM SNARF-5F or 4F;

Glucose stock: 0.5 M glucose in DI water;

Incubation buffers for pHrodo Green: PBS and 0.9% NaCl were mixed in volumetric ratio 1:3 and 1:5 (concentration of buffering ions ($HPO_4^{2-}$ and $H_2PO_4$) approximately 3 and 2 mM). 50 µL of glucose stock and 20 µL of dye stock solutions were added per each mL of the resulting buffer solution (final concentration 25 mM of glucose and 20 µg/ml of pHrodo Green);

Incubation buffer for SNARF-5F or 4F: HBSS, 10 mM glucose, Joklik's modified EMEM.

3. Cells

A549 cells (human lung carcinoma, Hubrecht lab) were cultures in DMEM (Dulbecco's Modified Eagle Medium, a culture medium) 10 min at +10% Fetal Bovine Serum, detached using 0.25% Trypsin-EDTA and re-suspended in the incubation buffer. Peripheral Blood Mononuclear Cells (PBMCs) were isolated by Ficoll (registered trade mark) density gradient separation. Buffy coat from complete blood with anticoagulant is taken and diluted approximately 4.5×. Ficoll is added under the blood and cells are spun down at Room Temperature for 25 min at 800 g. Interphase is removed and washed twice (10 min at 650 g, and 5 min at 550 g). Finally, cells are resuspended in serum free RPMI (Roswell Park Memorial Institute culture medium).

4. PDMS Device fabrication

Photolithography was used to fabricate masters for PDMS replication. 25 µm thick layer of SU8-2025 was spun on silicon wafer, baked, exposed through transparency mask, baked again and developed. The manufacturer's suggested processing conditions were used for the whole process.

PDMS prepolymer and crosslinking agent were mixed at a mass ratio of 10:1 (w/w); a mixture was poured onto a master, degassed and cured at 65 C for at least 2 h.

The replica was detached from master and reservoirs were bored using a blunt hypodermic needle. A PDMS replica was washed in soapy water and ethanol, and blow dried with nitrogen. A clean glass slide and a clean PDMS replica were treated with oxygen plasma and bonded. The device was silanized with 1% (Tridecafluoro-1,1,2,2-Tetrahydrooctyl)-1-Trichlorosilane in FC-40, which was introduced into microfluidic channels (enough to completely wet whole microfluidic network) and then the device was kept at 95 C for at least 30 min.

5. Detection

Observation of static droplets: An Olympus IX81 inverted epifluorescence microscope was used for fluorescence measurements. Microscope was equipped with xCite 120Q lamp (Lumen Dynamics Group Inc.), filter set and iXon 897 camera (Andor).

Observation of flowing droplets: As shown in FIG. 1, an Olympus IX71 inverted microscope was used to analyse flowing droplets one by one. A laser (Cube, Coherent Inc.) beam was expanded (~10×) and focused down at the middle of the detection channel. The fluorescence signal of excited droplets was detected by a PMT detector (H8249, Hamamatsu).

6. Detection of pH Change.

pH value was evaluated separately for cancerous cells and white blood cells. In one experiment 30 to 50 µL of cell suspension in the incubation buffer was emulsified in a T-junction microfluidic device (height: 25 µm; the widths of continuous and disperse phase channels were 20 µm). The disperse phase flow rate was 120 µL/h; the continuous phase flow rate was 600 µL/h. The emulsion was collected in a plastic vial and subsequently incubated at 37° C. for 1 h. For observation droplets were a) placed on microscope slide or b) injected in a microfluidic device. The detection was carried out by the PhrodoGreen or SNARF-5F or 4F. The first increases fluorescence while the pH lower, SNARF-schange their absorption spectrum while the pH changes and more in particular, increase fluorescence at 580 nm and decrease fluorescence at 640 nm when the pH decreases. Accordingly, the higher 580/630 ratio, the lower pH. Fluorescence was detected using an inverted epifluorescence microscope.

Results

Results are displayed in FIGS. 5 e 6 and in the table 1 below.

In particular, as already indicated above, higher 580/630 ratio, the lower pH. Cancer cells are in a range from 7.4 to 6.4 whereas white blood cells don't go below a pH of 7.0

TABLE 1

| 580/630 ratio | pH value |
|---|---|
| 1 | 7.4 |
| 1.5 | 7.0 |
| 2 | 6.8 |
| 2.5 | 6.6 |
| 3 | 6.4 |
| 3.5 | 6.2 |
| 4 | 6 |

TABLE 1-continued

| 580/630 ratio | pH value |
|---|---|
| 4.5 | 5.8 |
| 5 | 5.6 |
| 5.5 | 5.22 |

Figure 6A:
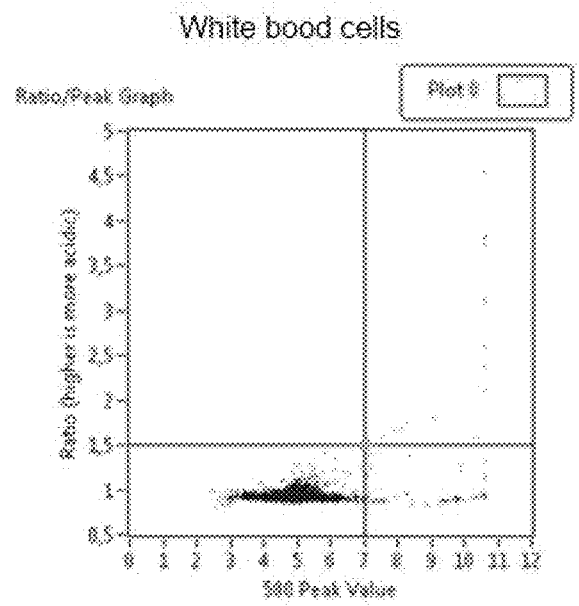
FIGS. 6A-6B show the different distribution of circulating ovarian cancer cells and white blood cells in a graph where 580/630 emission ratio (the higher ratio, the lower pH) is reported on the y-axis.
Figure 6B:
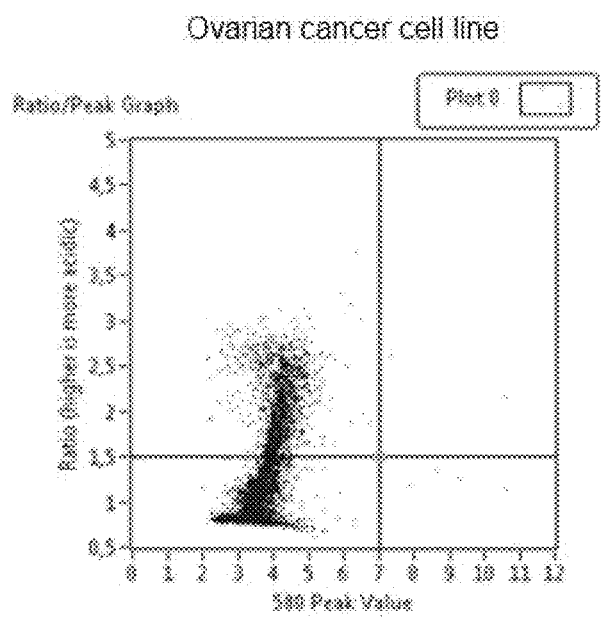

Referring to FIGS. 6A-6B, it can be appreciated that threshold of x<7 and y>1.5 offers 100% specificity in detecting cancer cells with respect to with blood cells.

7. Detection of Lactic Acid Secretion

Lactic acid secretion was evaluated using mixed suspensions of cancer cells (A549) and white blood cells from a red blood cells-lysed solution. A three-channel architecture microfluidic circuit was used: one channel bringing the cell suspension, one bringing the enzymes for lactate assay and one bringing oil phase. Emulsification step was performed at 4° C. to stop cell metabolism to avoid lactate contamination of the whole solution by cancer cells. With this microfluidic device we could expose cells to the enzymes of the lactate assay only after encapsulation in the micro-droplets, to avoid unspecific activation prior the encapsulation. Pictures were taken 15 minutes after emulsification, at room temperature.

Results

Figure 2A:
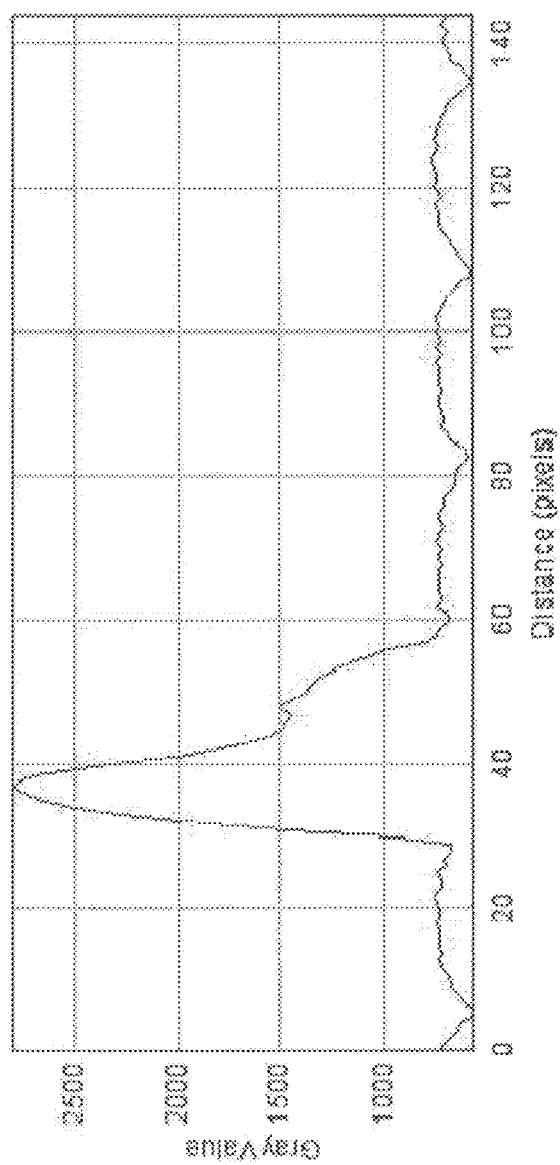
FIGS. 2a and 2b show, respectively, a fluorescence micrograph of a (stationary) closely packed emulsion in a microfluidic device, and a cross-section through a tumour (A549) cell contained within a droplet within a microfluidic device, illustrating fluorescence from the droplet.
Figure 2B:
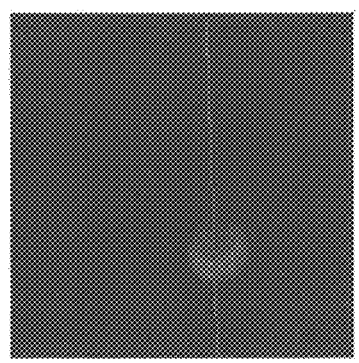
Figure 3:
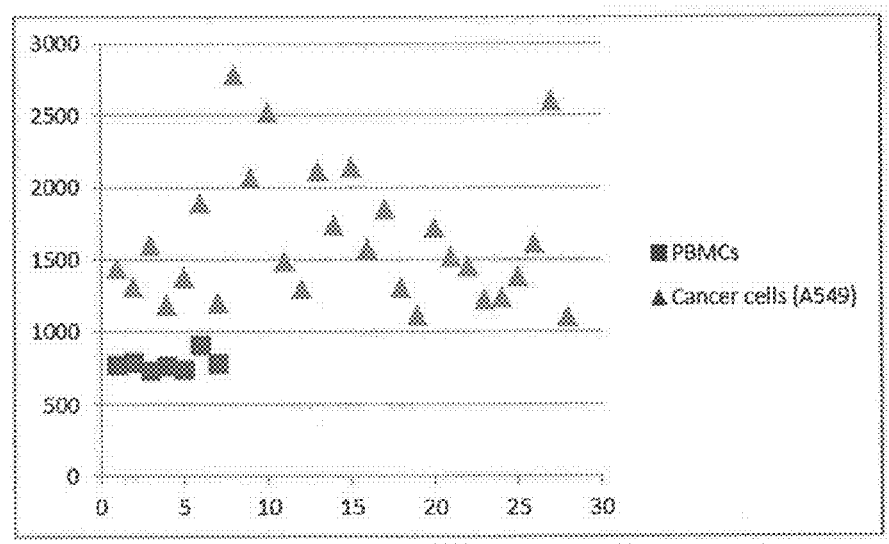
FIG. 3 shows a comparison of the fluorescence intensity from a pH-sensitive dye in droplets containing tumour cells (A549) and white blood cells (PBMCs), showing the average fluorescence intensity per droplet, dispersing data along the X axis to better visualize the data points.

The fluorescence due to pH change in the cell containing droplets is shown in FIG. 2. Droplets containing an A549 tumour cell are distinguishable from empty droplets. In a separate experiment PBMCs were incubated in presence of glucose. A comparison of A549 and PBMCs is shown in FIG. 3: Empty and cell containing droplets were manually selected from fluorescence micrographs, and measurements of empty droplets were included for comparison for both experiments. Both cell types show decrease in pH (increase in fluorescence intensity), but this is substantially more pronounced in the case of A549 tumour cells.

Figure 4:
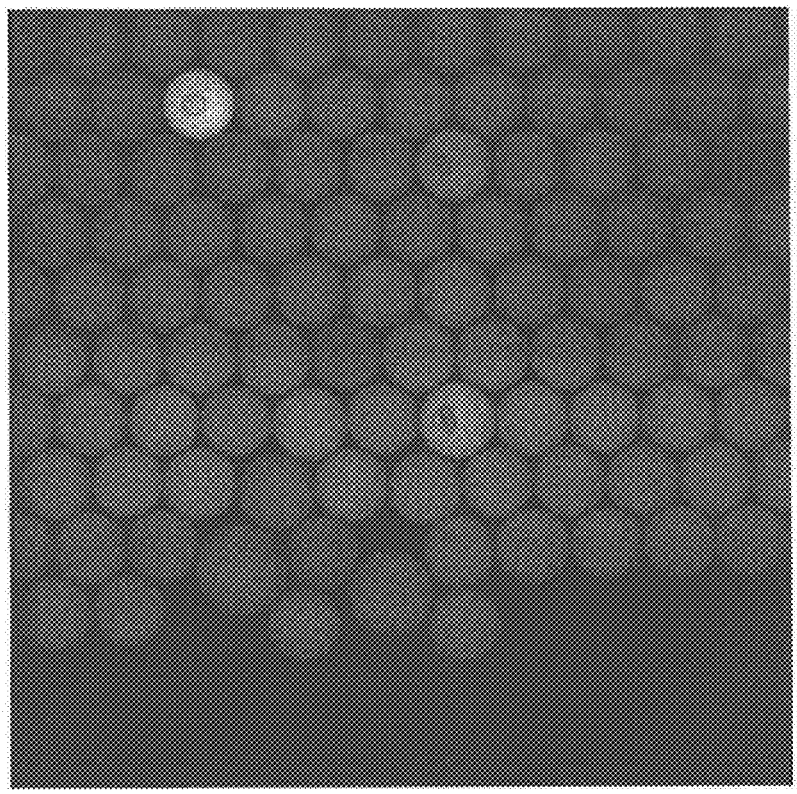
FIG. 4 Fluorescent enzymatic lactate assay. The top left, brighter droplet, is enclosing a cancer cell, the majority of droplets are empty, while the two droplets containing cells on the right are enclosing PBMCs (Peripheral blood mononuclear cells). Please note that more than one PBMC is present inside droplets, and this does not make the droplet brighter in comparison with droplets with just one single cancer cell.
Figure 5A:
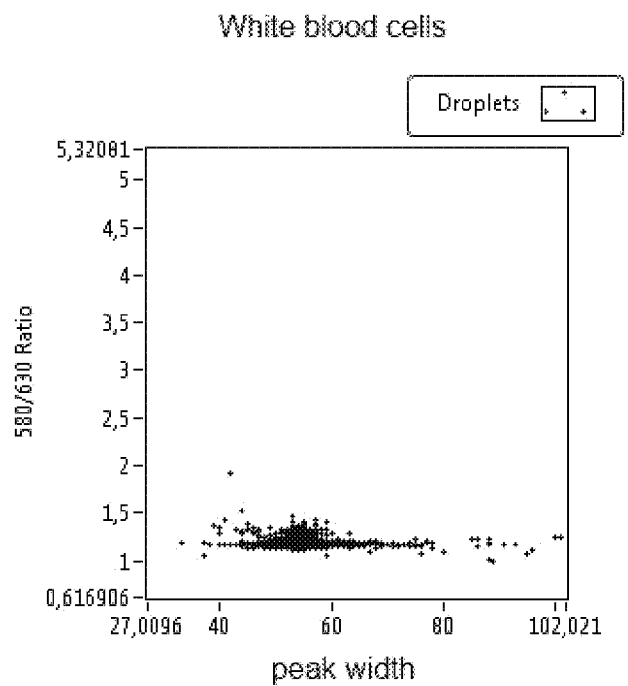
FIGS. 5A-5D show the different distribution of cancer cells and white blood cells in a graph where 580/630 emission ratio (the higher ratio, the lower pH) is reported on the y-axis and peak width on the x-axis. In particular, FIG. 5A refers to white blood cells.
Figure 5B:
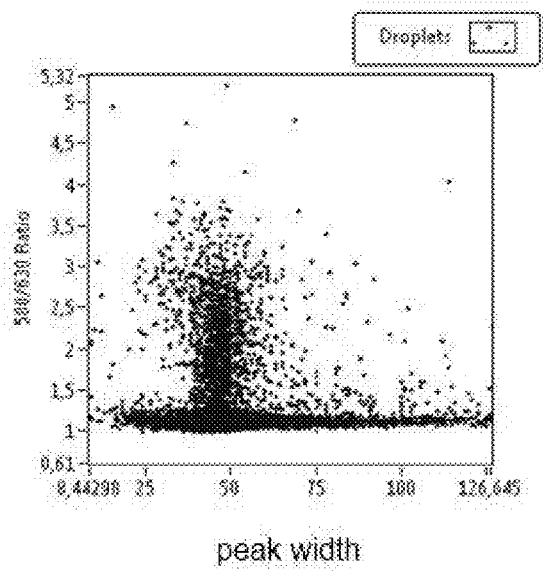
Figure 5C:
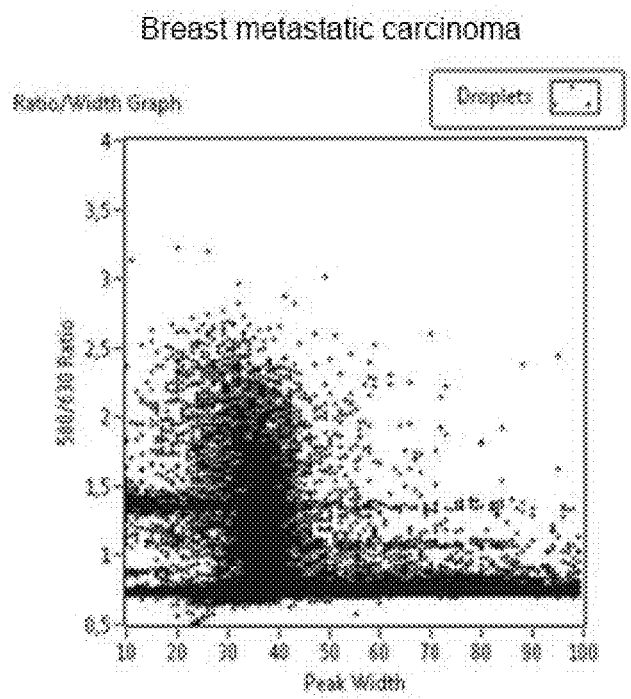
Figure 5D:
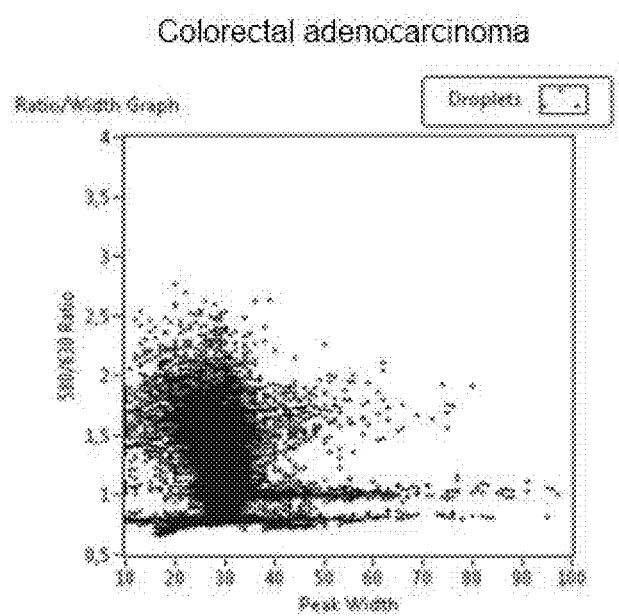

In the case of lactate assay, analogue results can be seen in FIG. 4.

It can therefore be appreciated that embodiments of the method described herein facilitate an antibody-free method for the detection and fast counting of CTCs. Embodiments of the method object of the present disclosure may be used for prognosis, therapy monitoring and theranostic applications. For example the method may be employed for stratification and/or real-time monitoring of therapies as well as for estimating the risk of metastatic relapse and/or metastatic progression.

The present invention has been described so far with reference to preferred embodiments. It is intended that there may be other embodiments which refer to the same inventive nucleus, all falling within the protection of the claims set out below.

The invention claimed is:

1. A method for detecting at least one circulating tumour cell in a body fluid comprising the following steps:
   encapsulating cells of said body fluid, wherein said cells are in an encapsulated volume of about 10 pL to 10 nL of said body fluid;
   incubating said encapsulated volume at a temperature from 4° C. to 37° C. for at least 1 minute to provide an incubated volume; and
   detecting a change in pH and/or in concentration of at least one molecule selected from the group consisting of lactic acid, lactate ions, and protons within said incubated volume; wherein a decrease in pH and/or an increase in concentration of said at least one molecule, with respect to pH and/or concentration of said at least one molecule determined for said encapsulated volume before said incubation step, indicates said at least one circulating tumour cell is present in said body fluid.

2. The method according to claim 1, wherein said encapsulated volume is in form of a droplet within a droplet-based microfluidic device.

3. The method according to claim 2, wherein said droplet is an aqueous droplet in a W/O emulsion.

4. The method according to claim 3, wherein said W/O emulsion has an oil component comprising a fluorous oil.

5. The method according to claim 1, further comprising a step of dilution of said encapsulated volume with water or a salt-containing buffer.

6. The method according to claim 5, wherein said oil component further comprises a surfactant.

7. The method according to claim 1, wherein said body fluid is selected from the group consisting of blood, serum, lymph, pleural fluid, peritoneal fluid, and cerebrospinal fluid.

8. The method according to claim 1, wherein said change in pH and/or in concentration of said at least one molecule is detected by using a pH-indicator and/or fluorescent indicator.

9. The method according to claim 8, wherein said pH-indicator is a pH-sensitive dye or an indicator that changes its adsorption/emission spectrum while the pH changes.

10. The method according to claim 9, further comprising a step of irradiating said incubated volume by a laser emitting at a visible wavelength, said change being a function of an emitted signal of said irradiated volume.

11. The method according to claim 1, wherein said step of incubation is carried out for at least 1 hour.

* * * * *